United States Patent
Ney et al.

(10) Patent No.: US 10,307,600 B2
(45) Date of Patent: *Jun. 4, 2019

(54) SYSTEM AND METHOD FOR INTERACTING WITH AN IMPLANTABLE MEDICAL DEVICE

(71) Applicant: Medtronic, Inc., Minneapolis, MN (US)

(72) Inventors: Corey E. Ney, Medina, MN (US); Kent D. Magaard, Wayzata, MN (US)

(73) Assignee: Medtronic, Inc., Minneapolis, MN (US)

( * ) Notice: Subject to any disclaimer, the term of this patent is extended or adjusted under 35 U.S.C. 154(b) by 25 days.

This patent is subject to a terminal disclaimer.

(21) Appl. No.: 14/861,466

(22) Filed: Sep. 22, 2015

(65) Prior Publication Data

US 2017/0080241 A1    Mar. 23, 2017

(51) Int. Cl.
| | | |
|---|---|---|
| *A61N 1/372* | (2006.01) | |
| *A61N 1/362* | (2006.01) | |
| *G06F 3/0354* | (2013.01) | |
| *G16H 40/63* | (2018.01) | |
| *G06F 19/00* | (2018.01) | |

(52) U.S. Cl.
CPC ......... *A61N 1/37247* (2013.01); *A61N 1/362* (2013.01); *A61N 1/37282* (2013.01); *G06F 3/0354* (2013.01); *G06F 19/00* (2013.01); *G16H 40/63* (2018.01)

(58) Field of Classification Search
CPC ............ A61N 1/37247; A61N 1/37252; A61N 1/3727

USPC ......................................... 607/30, 31, 32, 60
See application file for complete search history.

(56) References Cited

U.S. PATENT DOCUMENTS

| | | |
|---|---|---|
| 5,168,269 A | 12/1992 | Harlan |
| 5,654,726 A | 8/1997 | Mima et al. |
| 6,047,051 A * | 4/2000 | Ginzboorg ........... G06Q 20/102 235/380 |
| 6,325,756 B1 | 12/2001 | Webb et al. |
| 6,584,352 B2 | 6/2003 | Combs et al. |

(Continued)

FOREIGN PATENT DOCUMENTS

GB           2518206 A       3/2015

OTHER PUBLICATIONS (PCT/US2016/051682) PCT Notification of Transmittal of the International Search Report and the Written Opinion of the International Searching Authority, dated Jan. 10, 2017, 14 pages.

(Continued)

*Primary Examiner* — Christopher D Koharski
*Assistant Examiner* — Roland Dinga

(57) ABSTRACT

One example of a system includes a local user system to interact with an implantable medical device and a local input device communicatively coupled to the local user system to generate local events. To operate the local user system, the local user system is to receive and process local events from the local input device and receive and process remote events from a remote user system communicatively coupled to the local user system over a network communication link. The local user system is to monitor the network communication link and abort processing of a remote event in response to detecting a quality of service issue.

21 Claims, 7 Drawing Sheets

(56) References Cited

U.S. PATENT DOCUMENTS

| | | |
|---|---|---|
| 6,804,558 B2 | 10/2004 | Haller et al. |
| 7,060,031 B2 | 6/2006 | Webb et al. |
| 8,204,990 B1 | 6/2012 | Avery et al. |
| 8,319,728 B2 | 11/2012 | Geffin et al. |
| 8,589,489 B2 | 11/2013 | Bomgaars et al. |
| 2008/0015427 A1 | 1/2008 | Kastelein et al. |
| 2008/0091819 A1 | 4/2008 | Yang |
| 2008/0291930 A1 | 11/2008 | Damola et al. |
| 2009/0281598 A1 | 11/2009 | Haubrich et al. |
| 2010/0030303 A1* | 2/2010 | Haubrich ............... A61N 1/08 607/60 |
| 2010/0125174 A1* | 5/2010 | Bevan ................ G16H 80/00 600/300 |
| 2010/0223020 A1* | 9/2010 | Goetz ............... A61B 5/0031 702/104 |
| 2012/0026009 A1* | 2/2012 | Zhao ............... A61N 1/37229 340/870.28 |
| 2014/0002361 A1 | 1/2014 | Ballard et al. |
| 2014/0109002 A1 | 4/2014 | Kimball et al. |
| 2014/0244839 A1 | 8/2014 | Yoon et al. |

OTHER PUBLICATIONS (PCTUS2016/051645) PCT Notification of Transmittal of the International Search Report and the Written Opinion of the International Searching Authority, dated Dec. 14, 2016, 13 pages.
"Medtronic EnPulse Pacemaker Programming Guide", www.meenamedical.com/uploads/Manuals/EKG/Medtronic9790_programming_guide.pdf, retrieved on Dec. 6, 2016, May 2003, pp. 1-11 to 1-15.

\* cited by examiner

SYSTEM AND METHOD FOR INTERACTING WITH AN IMPLANTABLE MEDICAL DEVICE

BACKGROUND

Patients having Implantable Medical Devices (IMDs) may require periodic retrieval of information from the IMD to assess device operation and patient device monitoring history. A need may also arise to update software used by the IMD or to provide a therapy to a patient having an IMD. Retrieval of information from the IMD, programming of the IMD, or providing a therapy to a patient having an IMD is typically performed during a patient session. The patient session may be located at a clinic or other location, such as an implant center. During each patient session, both a clinician (e.g., device nurse/technician or physician) and a device representative from the company that supplied the IMD may be present. The clinician may aid the patient during the IMD information retrieval, programming, and/or therapy and the device representative may assure proper operation of the IMD. Given the number of patients with IMDs, these patient sessions are expensive.

SUMMARY

One example of a system includes a local user system to interact with an implantable medical device and a local input device communicatively coupled to the local user system to generate local events. To operate the local user system, the local user system is to receive and process local events from the local input device and receive and process remote events from a remote user system communicatively coupled to the local user system over a network communication link. The local user system is to monitor the network communication link and abort processing of a remote event in response to detecting a quality of service issue.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

To save time and reduce costs associated with Implantable Medical Device (IMD) patient sessions at clinics, a local user system may be located at the clinic visited by the patient while a remote user system may be located remote from the location of the patient. The local user system includes an IMD programmer, which may be operated by a clinician. The remote user system may be used to operate the IMD programmer from the remote location, thus eliminating the need for a remote user, such as an IMD device representative or physician, to travel to the clinic where the patient is located. Rather, the IMD device representative and/or physician may be located at the remote user system and may communicate directly with the clinician or patient via other means such as by telephone. Retrieval of information from an IMD, programming of an IMD, and/or the providing of a therapy via an IMD may be controlled either by the local user system or the remote user system.

The communication link between the local user system and the remote user system may be lost or become unstable during a clinic session while the IMD programmer is under the control of the remote user system. This lost or unstable communication link may put the patient in danger. To prevent this, the local user system monitors the communication link and aborts the processing of any remote event in response to detecting a quality of service issue with the communication link as described in the following description.

Figure 1:
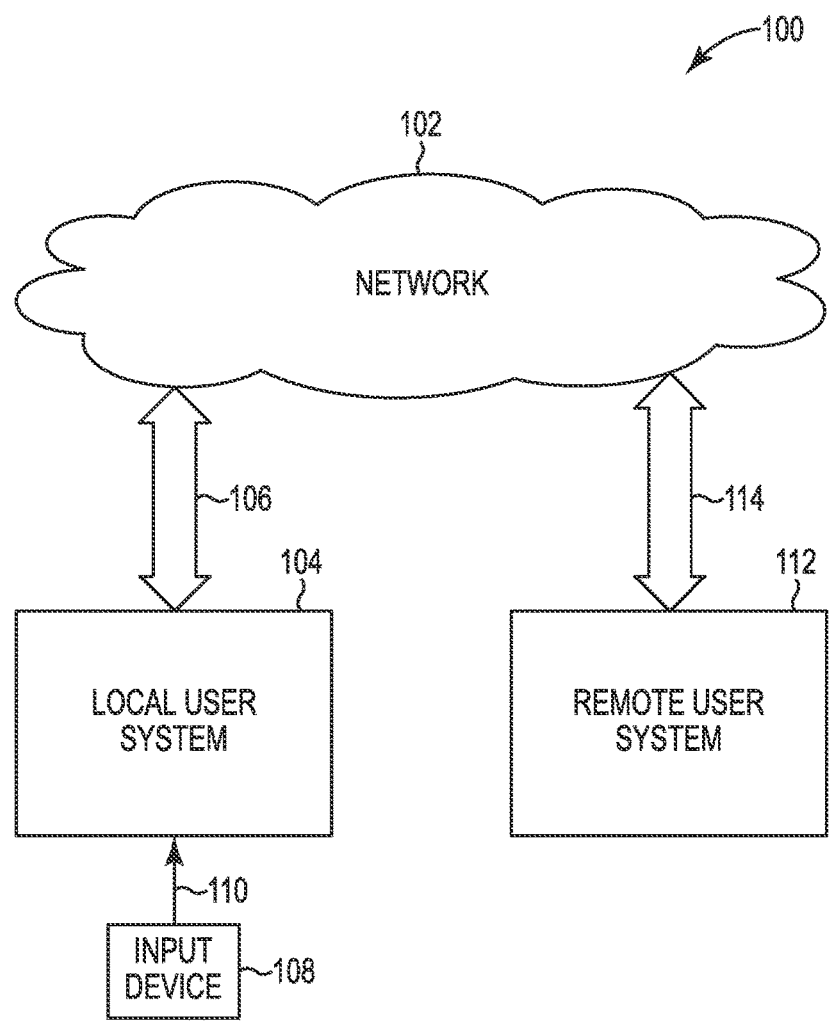
FIG. 1 is a block diagram illustrating one example of a system for interacting with an Implantable Medical Device (IMD).

FIG. 1 is a block diagram illustrating one example of a system 100 for interacting with an Implantable Medical Device (IMD). System 100 includes a network 102, a local user system 104, and a remote user system 112. Local user system 104 is communicatively coupled to network 102 through a communication link 106. Remote user system 112 is communicatively coupled to network 102 through a communication link 114. Remote user system 112 may be used to control local user system 104 through a network communication link between remote user system 112 and local user system 104 through network 102.

Local user system 104 includes hardware and software for interacting with an IMD (not shown). Local user system 104 may be used to interrogate an IMD, program an IMD, or provide a therapy to a patient via an IMD. An input device 108 is communicatively coupled to local user system 104 through a communication link 110. Input device 108 generates local events for controlling local user system 104 in response to a local user interacting with input device 108. For example, a local user may use input device 108 to generate a local event for interrogating an IMD, programming an IMD, or providing a therapy to a patient via an IMD.

Remote user system 112 includes hardware and software for controlling local user system 104. For example, a remote user may generate a remote event received by local user system 104 to interrogate an IMD, program an IMD, or provide a therapy to a patient via an IMD. Local user system 104 monitors the network communication link between remote user system 112 and local user system 104. In response to local user system 104 detecting a quality of service issue with the network communication link (e.g., lost connection, poor connection, intermittent connection), local user system 104 aborts the processing of any currently processing remote event. Local events generated by input device 108 may continue to be processed in response to detecting a quality of service issue with the network communication link.

Figure 2:
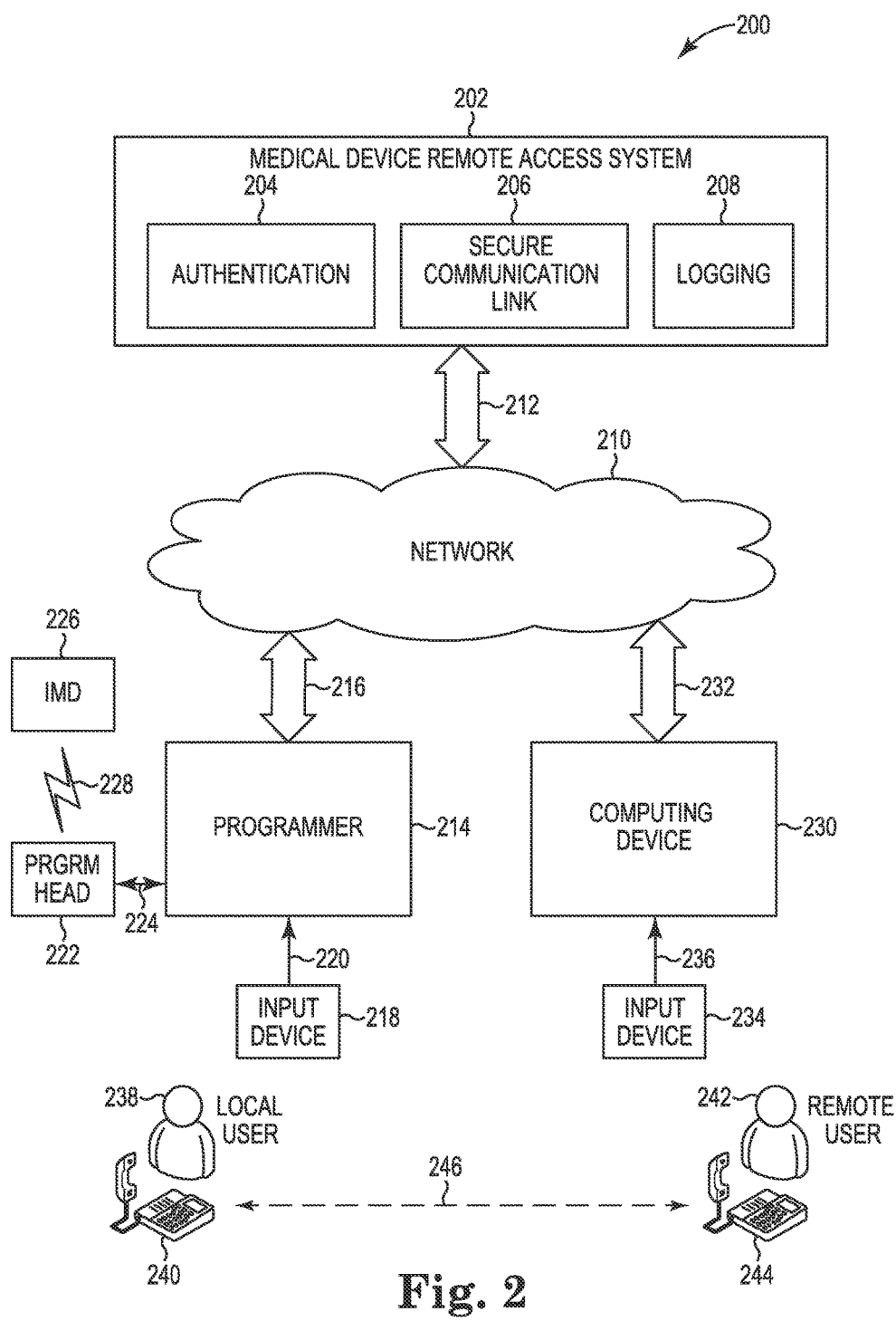
FIG. 2 is a block diagram illustrating another example of a system for interacting with an IMD.

FIG. 2 is a block diagram illustrating another example of a system 200 for interacting with an IMD 226. System 200 includes a medical device remote access system 202, a network 210, a programmer 214, and a computing device 230. In one example, programmer 214 provides local user system 104 and computing device 230 provides remote user system 112 previously described and illustrated with reference to FIG. 1. Medical device remote access system 202 is communicatively coupled to programmer 214 via a communication link 212, network 210, and a communication link 216. Medical device remote access system 202 is communicatively coupled to computing device 230 via communication link 212, network 210, and a communication link 232. In one example, network 210 is the Internet. In another example, network 210 is a wide area network, a local area network, or another suitable network.

Medical device remote access system 202 includes hardware and software to provide a variety of functions including, for example, device authentication 204, establishing a secure communication link 206, and data logging 208. In one example, medical device remote access system 202 is a server and may authenticate programmer 214 and computing device 230 in response to programmer 214 and computing device 230 requesting a connection for a patient session. In response to authenticating programmer 214 and computing device 230, medical device remote access system 202 may establish a secure communication link (e.g., Secure Socket Layer (SSL) channel) between programmer 214 and computing device 230. Medical device remote access system 202 may log data regarding session connections and actions and/or other suitable data related to a patient session.

Programmer 214 is a processing system for interacting with IMD 226 via a programming head 222. Programmer 214 may be a desktop computer, a laptop computer, a tablet computer, a mobile device, or another suitable processing system. Programming head 222 is communicatively coupled to programmer 214 through a communication link 224. In one example, communication link 224 is a wireless communication link (e.g., Bluetooth). Programming head 222 provides a wireless communication link 228 between programmer 214 and IMD 226 during a patient session. In one example, programming head 222 contains a strong permanent magnet and a Radio-Frequency (RF) transmitter and receiver. IMD 226 may include a pacemaker, a defibrillator, or another suitable implantable medical device.

A local input device 218 is communicatively coupled to programmer 214 through a communication link 220. In one example, input device 218 is integrated into programmer 214. Input device 218 may include a touch pen, a mouse, a touch pad, a touch screen, a keyboard, a keypad, or another suitable input device. Input device 218 is used to operate programmer 214 by generating local events in response to actions of a local user 238. Programmer 214 receives the local events generated by input device 218 and performs actions based on the local events.

For example, local user 238 may click a mouse button to generate a local mouse click event, which is received by programmer 214 for selecting a particular action based on the position of the mouse, such as to interrogate IMD 226 or to program IMD 226. In another example, local user 238 may press a mouse button down to generate a local mouse press down event, which is received by programmer 214 for starting delivery of a therapy to a patient via IMD 226. Local user 238 releases the mouse button to generate a local mouse up event, which is received by programmer 214 for stopping delivery of the therapy to the patient. As used herein, "mouse events" such as mouse click events, mouse move events, mouse press down events, and mouse up events are used to generally refer to events generated by any suitable input device and are not limited to events generated by a mouse. Other input devices that may generate "mouse events" as used herein may include, for example, touch pens, touch pads, touch screens, keyboards, and keypads.

Computing device 230 is a processing system for operating programmer 214 through network 210. Computing device 230 may be a desktop computer, a laptop computer, a tablet computer, a mobile device, or another suitable processing system. Computing device 230 emulates programmer 214 such that actions of a remote user 242 performed on computing device 230 are transmitted to programmer 214 for controlling programmer 214. A remote input device 234 is communicatively coupled to computing device 230 through a communication link 236. In one example, input device 234 is integrated into computing device 230. Input device 234 may include a touch pen, a mouse, a touch pad, a touch screen, a keyboard, a keypad, or another suitable input device. Input device 234 is used to operate programmer 214 by generating remote events in response to actions of remote user 242. Computing device 230 receives the remote events generated by input device 234 and transmits the remote events to programmer 214, which receives the remote events and performs actions based on the remote events.

For example, remote user 242 may click a mouse button to generate a remote mouse click event, which is received by programmer 214 for selecting a particular action based on the position of the mouse, such as to interrogate IMD 226 or to program IMD 226. In another example, remote user 242 may press a mouse button down to generate a remote mouse press down event, which is received by programmer 214 for starting delivery of a therapy to a patient via IMD 226. Remote user 242 releases the mouse button to generate a remote mouse up event, which is received by programmer 214 for stopping delivery of the therapy to the patient. During a patient session, local user 238 using a telephone 240 and remote user 242 using a telephone 244 may communicate with each other over a communication link 246, such as a telephone communication link. In this way, local user 238 and remote user 242 may coordinate with each other during the patient session.

Programmer 214 monitors the network communication link between computing device 230 and programmer 214. In response to programmer 214 detecting a quality of service issue with the network communication link such that remote control of programmer 214 by remote user 242 could result in an unsafe situation, programmer 214 aborts any currently processing remote event.

In one example, programmer 214 also prioritizes local events over remote events since the local user is with the patient and more aware of the patient's status. In response to programmer 214 receiving a local event and a remote event simultaneously, programmer 214 ignores the remote event and processes the local event. Programmer 214 aborts processing of a remote event in response to receiving a local event while the remote event is processing. Programmer 214 then processes the local event. Programmer 214 processes remote events as long as no local events are being processed and as long as the quality of service of the network communication link is at an acceptable level.

Figure 3:
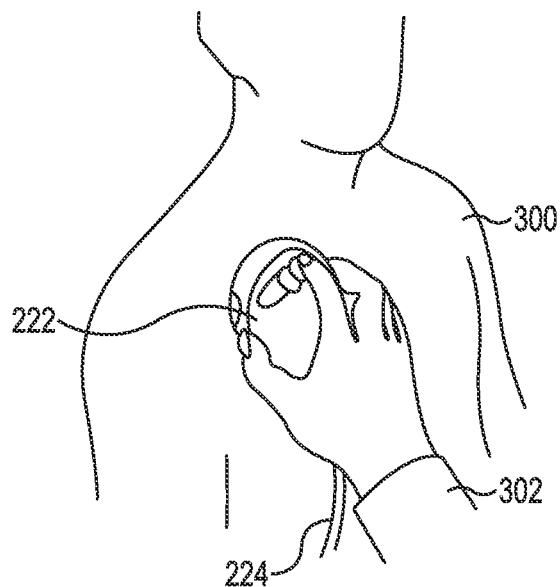
FIG. 3 illustrates one example of a programming head on a patient to interact with an IMD implanted in the patient.

FIG. 3 illustrates one example of a programming head 222 on a patient 300 to interact with an IMD (not shown) implanted in the patient 300. During a patient session, a clinician 302 holds programming head 222 over the IMD during a program, interrogate, or therapy operation. In one example, programming head 222 is held directly against the patient's skin with the face of programming head 222 parallel to and within two inches of the IMD. Correct placement of programming head 222 may be indicated by an array of lights (not shown) on programming head 222 and/or on a screen of programmer 214 (FIG. 2). In other examples, a shoulder strap containing the programming head is draped over the patient's shoulder, lining up the programming head 222 with the IMD.

Figure 4:
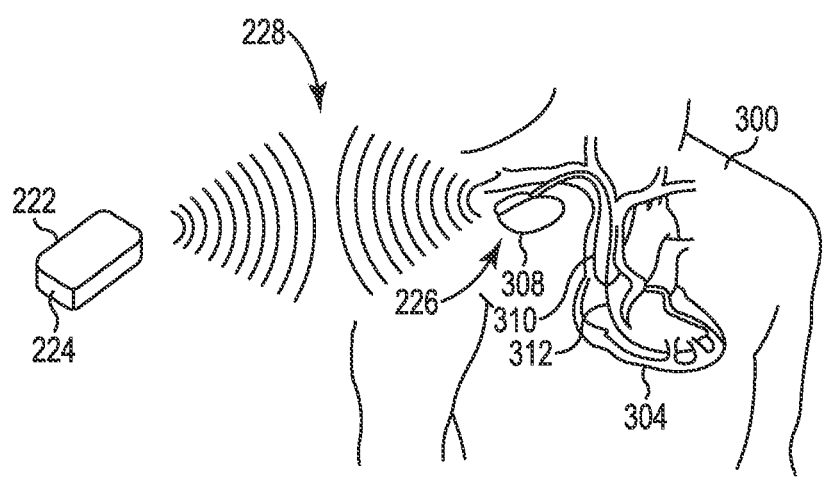
FIG. 4 illustrates one example of an IMD implanted in a patient and a wireless communication link between the IMD and a programming head.

FIG. 4 illustrates one example of an IMD 226 implanted in a patient 300 and a wireless communication link 228 between IMD 226 and programming head 222. In this example, IMD 226 is a pacemaker including at least one of pacing and sensing leads 310 and 312 attached to a hermetically sealed enclosure 308 near a heart 304 of patient 300. Pacing and sensing leads 310 and 312 sense electrical signals attendant to the depolarization and re-polarization of heart 304, and further provide pacing pulses for causing depolarization of cardiac tissue in the vicinity of the distal ends of the leads. Leads 310 and 312 may have unipolar or bipolar electrodes disposed thereon. Enclosure 308 encloses circuitry for operating IMD 226 including an RF transmitter and receiver for communicating with programming head 222 over wireless communication link 228. While FIG. 4 illustrates one example of an IMD 226 including a pacemaker, in other examples IMD 226 may be another suitable implantable medical device, such as a defibrillator.

Figure 5:
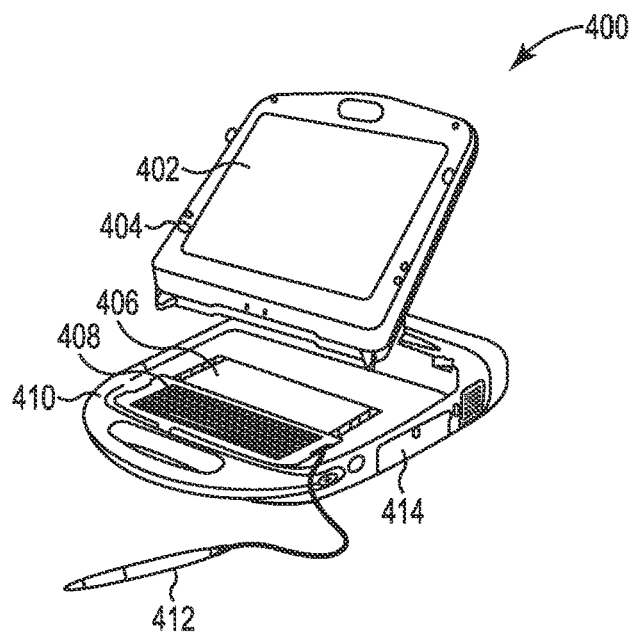
FIG. 5 illustrates one example of a local user system.

FIG. 5 illustrates one example of a local user system 400. In one example, local user system 400 provides local user system 104 previously described and illustrated with reference to FIG. 1 or programmer 214 previously described and illustrated with reference to FIG. 2. Local user system 400 may include a display screen 402, an emergency VVI button 404, a keyboard cover 406, a keyboard 408, printer controls 410, a touch pen 412 (e.g., a light pen), and a disk drive and/or PC card cover 414. Local user system 400 also includes a programming head (not shown).

Display screen 402 may be positioned smoothly from a closed position to a nearly horizontal position. Programming options may be selected on display screen 402 with touch pen 412. Predetermined options may be selected by applying touch pen 412 to display screen 402. Emergency VVI button 404 may be used to deliver a bradycardia VVI operation to a patient's IMD. Keyboard cover 406 may be slid forward to protect keyboard 408 or slid backward to expose keyboard 408. Keyboard 408 may be used to enter information into local user system 400. Printer controls 410 may be used to select a paper speed, start and stop printing, and advance the paper of a printer (not shown) integrated into local user system 400. Disk drive and/or PC card cover 414 may provide access to a disk drive and/or PC card, USB port, and/or integrated Ethernet.

In addition, local user system 400 may also include a microphone jack, a headphone jack, a telephone cord to connect a modem of local user system 400 to a telephone jack, electrode leads and an ECG cable to connect to skin electrodes on a patient for ECG and measurement functions requiring surface detection of cardiac and IMD signals, a power cord for connecting local user system 400 to an AC power outlet, and an Ethernet cable to connect local user system 400 to a clinic's network. In other examples, local user system 400 may include a battery for powering local user system 400 and may include a network interface for wirelessly connecting to a clinic's network.

In one example, local user system 400 is a Medtronic programmer. In other examples, local user system 400 includes other suitable components for interacting with an IMD. While local user system 400 illustrated in FIG. 5 uses touch pen 412 as an input device, in other examples local user system 400 uses a mouse, a touch pad, a touch screen, a keypad, or another suitable input device in place of or in addition to touch pen 412.

Figure 6:
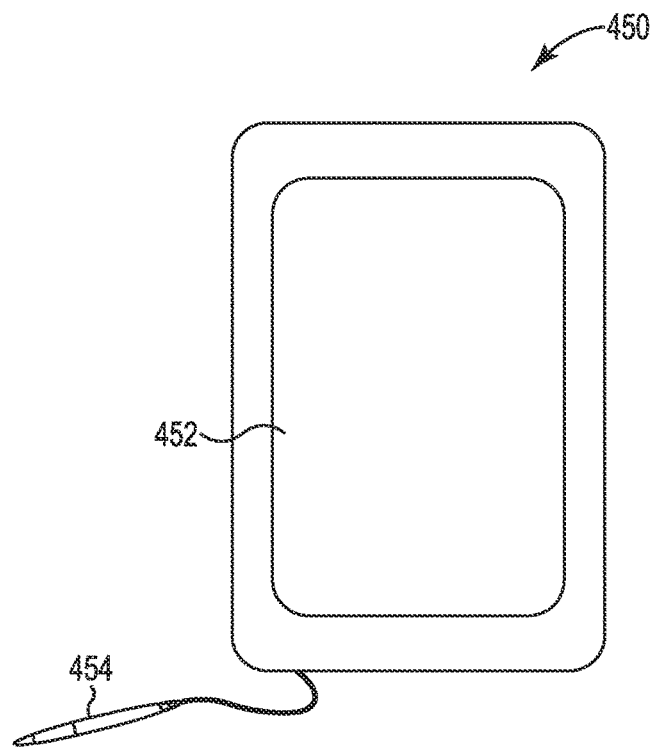
FIG. 6 illustrates one example of a remote user system.

FIG. 6 illustrates one example of a remote user system 450. In one example, remote user system 450 provides remote user system 112 previously described and illustrated with reference to FIG. 1 or computing device 230 previously described and illustrated with reference to FIG. 2. In this example, remote user system 450 is a tablet computer. In other examples, remote user system 450 may be a desktop computer, a laptop computer, or another suitable computing device.

Remote user system 450 may include a display screen 452 and a touch pen 454 (e.g. a light pen). In one example, during a patient session, display screen 452 emulates display 402 of local user device 400 (FIG. 5) by displaying the same information and options as display screen 402. Programming options may be selected on display screen 452 with touch pen 454. Predetermined options may be selected by applying touch pen 454 to display screen 452. While remote user system 450 illustrated in FIG. 6 uses touch pen 454 as an input device, in other examples remote user system 450 uses a mouse, a touch pad, a touch screen, a keyboard, a keypad, or another suitable input device in place of or in addition to touch pen 454.

Figure 7:
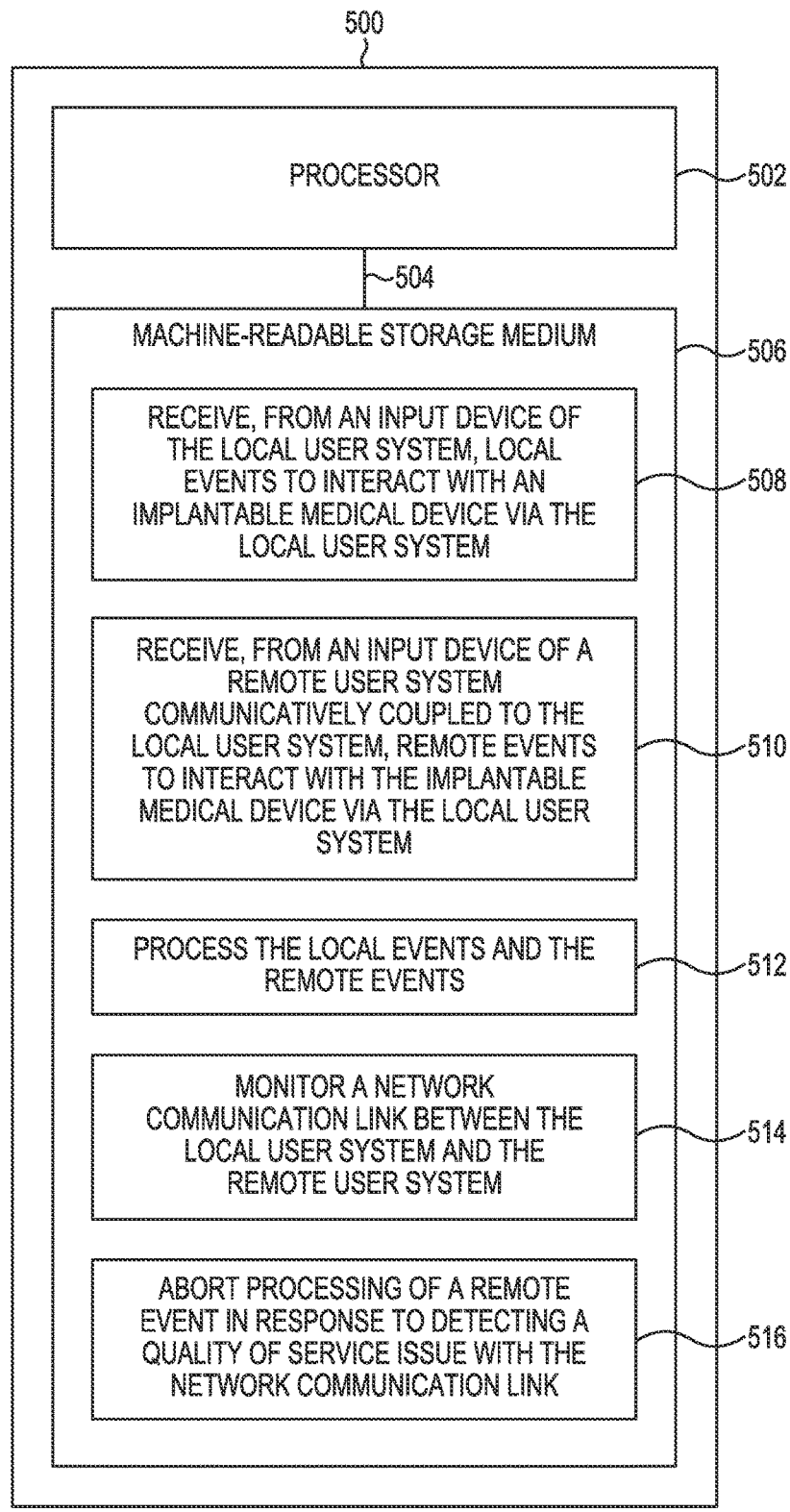
FIG. 7 is a block diagram illustrating one example of a processing system of a local user system for interacting with an IMD.

FIG. 7 is a block diagram illustrating one example of a processing system 500 of a local user system for interacting with an IMD. System 500 may include at least one computing device and may provide local user system 104 previously described and illustrated with reference to FIG. 1 or programmer 214 previously described and illustrated with reference to FIG. 2. System 500 includes a processor 502 and a machine-readable storage medium 506. Processor 502 is communicatively coupled to machine-readable storage medium 506 through a communication path 504. Although the following description refers to a single processor and a single machine-readable storage medium, the description may also apply to a system with multiple processors and multiple machine-readable storage mediums. In such examples, the instructions may be distributed (e.g., stored) across multiple machine-readable storage mediums and the instructions may be distributed (e.g., executed by) across multiple processors.

Processor 502 includes one or more Central Processing Units (CPUs), microprocessors, and/or other suitable hardware devices for retrieval and execution of instructions stored in machine-readable storage medium 506. Processor 502 may fetch, decode, and execute instructions 508 to receive local events, instructions 510 to receive remote events, instructions 512 to process events, instructions 514 to monitor a network communication link, and instructions 516 to abort processing of a remote event in response to detecting a quality of service issue. As an alternative or in addition to retrieving and executing instructions, processor 502 may include one or more electronic circuits comprising a number of electronic components for performing the functionality of one or more of the instructions in machine-readable storage medium 506. With respect to the executable instruction representations (e.g., boxes) described and illustrated herein, it should be understood that part or all of the executable instructions and/or electronic circuits included within one box may, in alternate examples, be included in a different box illustrated in the figures or in a different box not shown.

Machine-readable storage medium 506 is a non-transitory storage medium and may be any suitable electronic, magnetic, optical, or other physical storage device that stores executable instructions. Thus, machine-readable storage medium 506 may be, for example, Random Access Memory (RAM), an Electrically-Erasable Programmable Read-Only Memory (EEPROM), a storage drive, an optical disc, and the like. Machine-readable storage medium 506 may be disposed within system 500, as illustrated in FIG. 7. In this case, the executable instructions may be installed on system 500. Alternatively, machine-readable storage medium 506 may be a portable, external, or remote storage medium that allows system 500 to download the instructions from the portable/external/remote storage medium. In this case, the executable instructions may be part of an installation package.

Machine-readable storage medium 506 stores instructions to be executed by a processor (e.g., processor 502) including instructions 508, 510, 512, 514, and 516 to operate system 500. Processor 502 may execute instructions 508 to receive, from an input device (e.g., input device 218 of FIG. 2) of the local user system (e.g., programmer 214 of FIG. 2), local events (e.g., mouse move events, mouse press down events, mouse up events) to interact with an implantable medical device (e.g., IMD 226 of FIG. 2) via the local user system. Processor 502 may execute instructions 510 to receive, from an input device (e.g., input device 234 of FIG. 2) of a remote user system (e.g., computing device 230 of FIG. 2) communicatively coupled to the local user system, remote events (e.g., mouse move events, mouse press down events, mouse up events) to interact with the implantable medical device via the local user system. Processor 502 may execute instructions 512 to process the local events and the remote events. Processor 502 may execute instructions 514 to monitor a network communication link between the local user system and the remote user system. Processor 502 may execute instructions 516 to abort processing of a remote event in response to detecting a quality of service issue with the network communication link.

In one example, processor 502 may also execute instructions to process remote events in response to not detecting a quality of service issue with the network communication link. Processor 502 may execute instructions to determine whether a local event or a remote event has been received; in response to determining that a remote event has been received, reset a watchdog time and process the remote event. Processor 502 may execute instructions to abort processing of the remote event in response to a difference between a current time and the watchdog time exceeding a threshold. Processor 502 may execute instructions to continue to process the remote event in response to a difference between a current time and the watchdog time not exceeding a threshold. Processor 502 may also execute instructions to interrogate the implantable medical device in response to a first event; program the implantable medical device in response to a second event; and provide a therapy to a patient via the implantable medical device in response to a third event.

Figure 8:
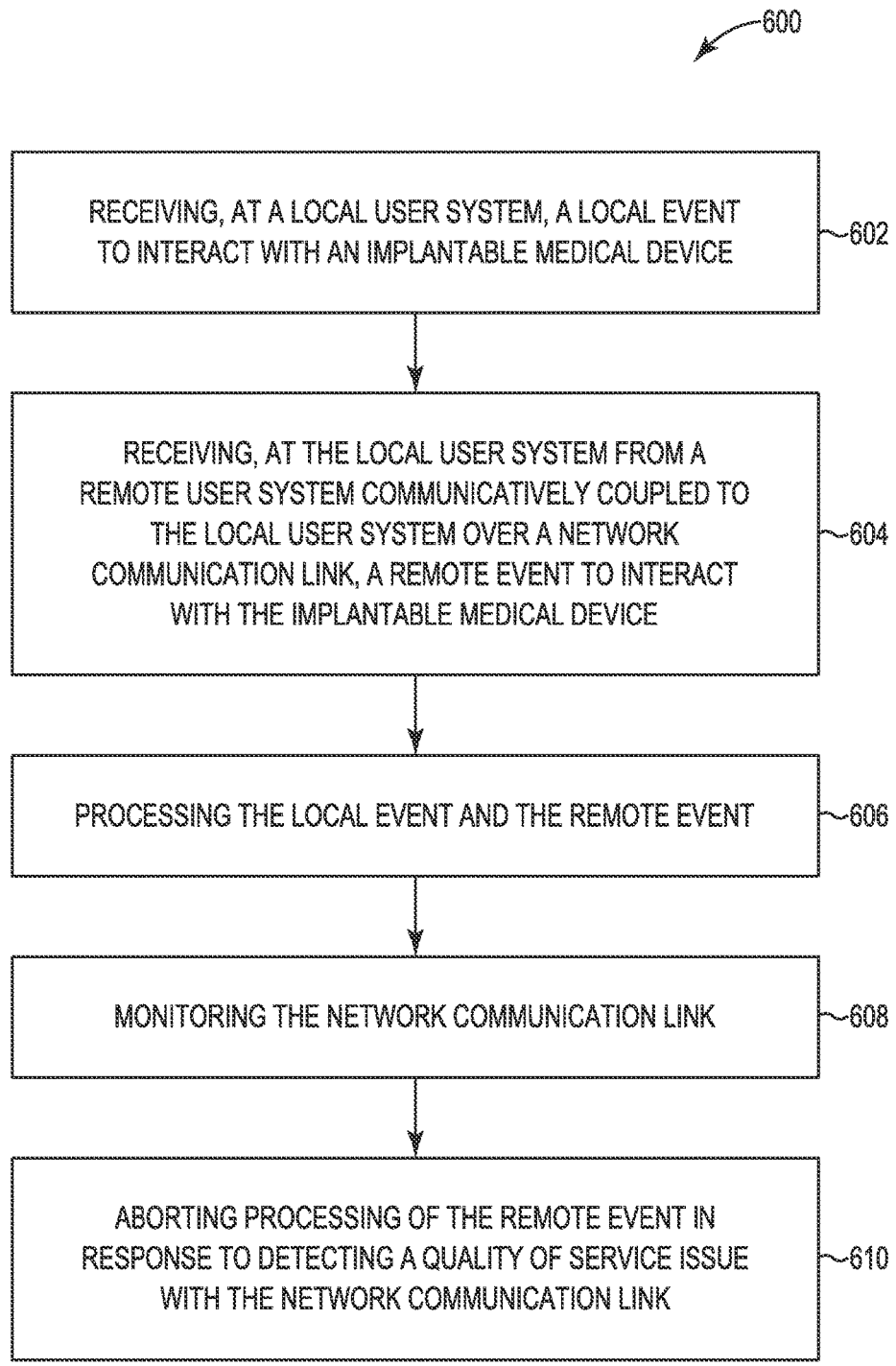
FIG. 8 illustrates one example of a process for interacting with an IMD.

FIG. 8 illustrates one example of a process 600 for interacting with an IMD. In one example, process 600 is implemented by local user system 104 previously described and illustrated with reference to FIG. 1 or programmer 214 previously described and illustrated with reference to FIG. 2. At 602, process 600 includes receiving, at a local user system, a local event to interact with an implantable medical device. At 604, process 600 includes receiving, at the local user system from a remote user system communicatively coupled to the local user system over a network communication link, a remote event to interact with the implantable medical device. At 606, process 600 includes processing the local event and the remote event. At 608, process 600 includes monitoring the network communication link. At 610, process 600 includes aborting processing of the remote event in response to detecting a quality of service issue with the network communication link.

In one example, process 600 includes continuing processing the remote event in response to not detecting a quality of service issue with the network communication link. Process 600 may also include aborting the processing of the remote event in response to receiving the local event while the remote event is processing. Receiving the local event may include receiving the local event from a local mouse and receiving the remote event may include receiving the remote event from a remote mouse. Process 600 may further include determining whether a local mouse event or a remote mouse event has been received; in response to determining that a remote mouse event has been received, resetting a watchdog time; comparing a difference between a current time and the watchdog time to a threshold; in response to the difference exceeding the threshold indicating a quality of service issue, determining whether the remote mouse is in a mouse press down state. In response to determining that the remote mouse is in a mouse press down state, changing, at the local user system, the remote mouse to a mouse up state. In response to determining that the remote mouse is not in a mouse press down state, ignoring the quality of service issue. Process 600 may also include communicating via telephone communications between a local user at the local user system and a remote user at the remote user system.

Figure 9:
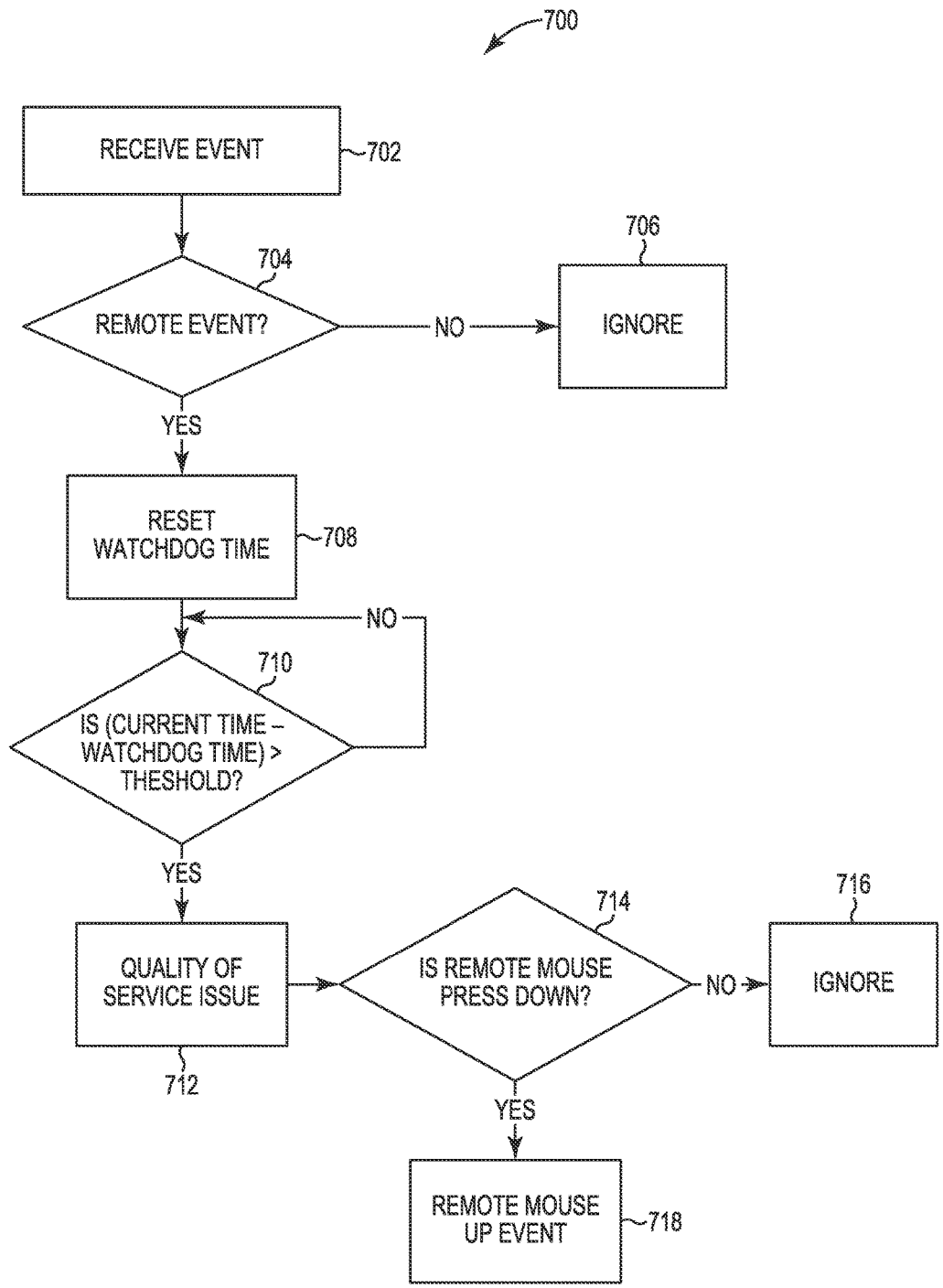
FIG. 9 illustrates one example of a process for monitoring a network communication link.

FIG. 9 illustrates one example of a process 700 for monitoring a network communication link. In one example, process 700 is implemented by local user system 104 previously described and illustrated with reference to FIG. 1 or programmer 214 previously described and illustrated with reference to FIG. 2. At 702, an event, such as a local or remote event (e.g., a local or remote mouse press down event, mouse up event, mouse move event, mouse active event) is received. At 704, it is determined whether the received event is a remote event. If the event is not a remote event (i.e., the event is a local event), then at 706 the event is ignored. If the event is a remote event, then at 708 a watchdog time is reset. In one example, the watchdog time is reset by setting the watchdog time to the current time.

At 710, it is determined whether the current time minus the watchdog time is greater than a threshold. In one example, the threshold is two seconds or another suitable period. If the difference between the current time and the watchdog time is less than the threshold, then 710 repeats. In one example, 710 repeats every 100 milliseconds or another suitable period. If a new remote event is received while 710 is repeating, the watchdog time is reset at 708 and the process continues at 710. If the difference between the current time and watchdog time is greater than the threshold at 710, then at 712 a quality of service issue is indicated. According, in this example, a quality of service issue with the network communication link is indicated in response to the local user system not receiving a remote event within a period set by the threshold. The remote event may be a mouse click event, a mouse press down event, a mouse up event, a mouse move event, a mouse active event, or another suitable event generated by a remote user system. A mouse active event may continue to be sent from the remote user system to the local user system even when the remote user is not interacting with the mouse (or other input device).

When a quality of service issue is detected, at 714 it is determined whether the remote mouse is in a mouse press down state (i.e., a remote event such as a therapy is in process). If the remote mouse is not in a mouse press down state, then at 716 the quality of service issue is ignored. If the remote mouse is in a mouse press down state at 714, then at 718 the remote mouse state is changed to a mouse up state by generating a remote mouse up event within the local user system. Generating the remote mouse up event aborts the processing of the remote mouse press down event. In this way, remote control of the local user system by a remote user system is aborted when a quality of service issue with the network communication link is detected.

Examples of the disclosure ensure that processing of a remote event is aborted in response to the local user system detecting a quality of service issue with the network communication link between the local user system and the remote user system. While the remote user system enables remote users to interact with an IMD of a patient without having to travel to the clinic where the patient is located thereby reducing costs, the monitoring of the network communication link and the aborting of remote events in response to a quality of service issue ensures patient safety during the patient session.

Although examples disclosed in this specification describe a local user system being located at a clinic, it is recognized that the local user system may be used for patient sessions at other locations. For example, a patient session may take place at an implant center.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A system comprising:
a local user system to interact with an implantable medical device; and
a local input device communicatively coupled to the local user system to generate local events to program or interrogate the implantable medical device;
wherein, to operate the local user system, the local user system is to receive and process local events from the local input device and receive and process remote events to program or interrogate the implantable medical device from a remote user system communicatively coupled to the local user system over a network communication link, and
the local user system to monitor the network communication link and abort processing of a remote event in response to detecting a quality of service issue with the network communication link.

2. The system of claim 1, wherein a local event comprises a mouse down event, a mouse up event, or a mouse move event, and
wherein a remote event comprises a mouse down event, a mouse up event, or a mouse move event.

3. The system of claim 1, wherein the remote user system comprises a remote input device to generate remote events.

4. The system of claim 1, wherein the local user system comprises:
a programming head to provide a wireless communication link to the implantable medical device; and
a programmer communicatively coupled to the programming head, the programmer to program and interrogate the implantable medical device via the programming head.

5. The system of claim 1, wherein the local input device comprises a touch pen.

6. The system of claim 1, wherein the remote user system comprises:
a computing device to emulate the local user system; and
a remote input device communicatively coupled to the computing device, the remote input device to generate remote events.

7. The system of claim 1, further comprising:
a medical device remote access system communicatively coupled to the local user system and the remote user system via the network communication link, the medical device remote access system comprising a server to authenticate the local user system and the remote user system and to establish a secure communication link between the local user system and the remote user system.

8. The system of claim 7, wherein the local user system and the remote user system are communicatively coupled to the medical device remote access system through the Internet.

9. A non-transitory machine-readable storage medium encoded with instructions, the instructions executable by a processor of a local user system to cause the local user system to:
receive, from an input device of the local user system, local events to interact with an implantable medical device via the local user system to interrogate the implantable medical device, program the implantable medical device, or deliver a therapy to a patient via the implantable medical device;
receive, from an input device of a remote user system communicatively coupled to the local user system, remote events to interact with the implantable medical device via the local user system to interrogate the implantable medical device, program the implantable medical device, or deliver a therapy to a patient via the implantable medical device;
process the local events and the remote events;
monitor a network communication link between the local user system and the remote user system; and
abort processing of a remote event in response to detecting a quality of service issue with the network communication link.

10. The non-transitory machine-readable storage medium of claim 9, wherein the instructions are executable by the processor to further cause the local user system to:
process remote events in response to not detecting a quality of service issue with the network communication link.

11. The non-transitory machine-readable storage medium of claim 9, wherein the instructions are executable by the processor to further cause the local user system to:
determine whether a local event or a remote event has been received;

in response to determining that a remote event has been received, reset a watchdog time and process the remote event; and abort processing of the remote event in response to a difference between a current time and the watchdog time exceeding a threshold.

12. The non-transitory machine-readable storage medium of claim 9, wherein the instructions are executable by the processor to further cause the local user system to:

determine whether a local event or a remote event has been received;

in response to determining that a remote event has been received, reset a watchdog time and process the remote event; and continue to process the remote event in response to a difference between a current time and the watchdog time not exceeding a threshold.

13. The non-transitory machine-readable storage medium of claim 9, wherein the instructions are executable by the processor to further cause the local user system to:

interrogate the implantable medical device in response to a first event;

program the implantable medical device in response to a second event; and provide a therapy to a patient via the implantable medical device in response to a third event.

14. A method comprising:

receiving, at a local user system, a local event to interact with an implantable medical device to interrogate the implantable medical device, program the implantable medical device, or deliver a therapy to a patient via the implantable medical device;

receiving, at the local user system from a remote user system communicatively coupled to the local user system over a network communication link, a remote event to interact with the implantable medical device to interrogate the implantable medical device, program the implantable medical device, or deliver a therapy to a patient via the implantable medical device;

processing the local event and the remote event;

monitoring the network communication link; and aborting processing of the remote event in response to detecting a quality of service issue with the network communication link.

15. The method of claim 14, further comprising:

continue processing the remote event in response to not detecting a quality of service issue with the network communication link.

16. The method of claim 15, further comprising:

aborting the processing of the remote event in response to receiving the local event while the remote event is processing.

17. The method of claim 14, wherein receiving the local event comprises receiving the local event from a local mouse, and wherein receiving the remote event comprises receiving the remote event from a remote mouse.

18. The method of claim 17, further comprising:

determining whether a local mouse event or a remote mouse event has been received;

in response to determining that a remote mouse event has been received, resetting a watchdog time;

comparing a difference between a current time and the watchdog time to a threshold;

in response to the difference exceeding the threshold indicating a quality of service issue, determining whether the remote mouse is in a mouse press down state;

in response to determining that the remote mouse is in a mouse press down state, changing, at the local user system, the remote mouse to a mouse up state.

19. The method of claim 17, further comprising:

determining whether a local mouse event or a remote mouse event has been received;

in response to determining that a remote mouse event has been received, resetting a watchdog time;

comparing a difference between a current time and the watchdog time to a threshold;

in response to the difference exceeding the threshold indicating a quality of service issue, determining whether the remote mouse is in a mouse press down state;

in response to determining that the remote mouse is not in a mouse press down state, ignoring the quality of service issue.

20. The method of claim 14, further comprising:

communicating via telephone communications between a local user at the local user system and a remote user at the remote user system.

21. A system comprising:

a local user system including a programmer, to interact with an implantable medical device via a wireless communication link; and a local input device communicatively coupled to the local user system to generate local events to interrogate the implantable medical device, program the implantable medical device, or deliver a therapy to a patient via the implantable medical device;

wherein, to operate the local user system, the local user system is to receive and process local events from the local input device and receive and process remote events to interrogate the implantable medical device, program the implantable medical device, or deliver a therapy to a patient via the implantable medical device from a remote user system, and the local user system to monitor a network communication link between the local user system and the remote user system, and abort processing of a remote event and only process local events in response to detecting a quality of service issue with the network communication link.

* * * * *